(12) United States Patent
Mousa

(10) Patent No.: US 8,968,790 B2
(45) Date of Patent: Mar. 3, 2015

(54) NANOFORMULATION OF VITAMIN D DERIVATIVES AND/OR VITAMIN D METABOLITES

(71) Applicant: Shaker A. Mousa, Wynantskill, NY (US)

(72) Inventor: Shaker A. Mousa, Wynantskill, NY (US)

( * ) Notice: Subject to any disclaimer, the term of this patent is extended or adjusted under 35 U.S.C. 154(b) by 0 days.

(21) Appl. No.: 13/706,755

(22) Filed: Dec. 6, 2012

(65) Prior Publication Data

US 2013/0149385 A1 Jun. 13, 2013

Related U.S. Application Data

(60) Provisional application No. 61/568,674, filed on Dec. 9, 2011.

(51) Int. Cl.
| | | |
|---|---|---|
| *A61K 9/14* | (2006.01) | |
| *A61K 9/16* | (2006.01) | |
| *A61K 9/51* | (2006.01) | |
| *A61K 47/48* | (2006.01) | |
| *B82Y 5/00* | (2011.01) | |

(52) U.S. Cl.
CPC ......... *A61K 9/5161* (2013.01); *A61K 47/48038* (2013.01); *A61K 47/4823* (2013.01); *Y10S 977/773* (2013.01); *Y10S 977/906* (2013.01); *B82Y 5/00* (2013.01)
USPC ........... 424/490; 424/489; 424/491; 977/773; 977/906

(58) Field of Classification Search
None
See application file for complete search history.

(56) References Cited

U.S. PATENT DOCUMENTS

| | | | |
|---|---|---|---|
| 6,465,626 B1* | 10/2002 | Watts et al. ...................... 536/20 |
| 8,563,053 B2* | 10/2013 | Mousa et al. .................. 424/755 |
| 2004/0247632 A1 | 12/2004 | Cattaneo | |
| 2005/0226905 A1* | 10/2005 | Tien et al. ...................... 424/439 |
| 2006/0034851 A1 | 2/2006 | Mazess et al. | |
| 2008/0200948 A1* | 8/2008 | Utecht et al. .................. 606/214 |
| 2008/0254078 A1 | 10/2008 | Kauper et al. | |
| 2008/0292713 A1 | 11/2008 | Seville et al. | |
| 2009/0074824 A1 | 3/2009 | VilaPena et al. | |
| 2010/0112162 A1 | 5/2010 | Tritsch et al. | |
| 2010/0158998 A1* | 6/2010 | Fox et al. ...................... 424/452 |
| 2011/0014135 A1 | 1/2011 | Buchta et al. | |
| 2011/0104230 A1 | 5/2011 | Mousa et al. | |
| 2011/0104265 A1 | 5/2011 | Mousa et al. | |
| 2011/0104283 A1 | 5/2011 | Mousa et al. | |
| 2011/0142890 A1 | 6/2011 | Fernandez et al. | |

FOREIGN PATENT DOCUMENTS

| | | | |
|---|---|---|---|
| WO | WO 03059358 A1 * | 7/2003 |
| WO | WO 2011063952 | 6/2011 |

OTHER PUBLICATIONS

Niu et al., "Porous nano-HA/collagen/PLLA scaffold containing chitosan microspheres for controlled delivery of synthetic peptide derived from BMP-2", Journal of Controlled Release 134 (2009), 111-117.*
Chen et al., "Preparation of Alginate/Poly(L-Arginine)-Chitosan ternary complex Microcapsules", Journal of Biomimetics, Biomaterials and Tissue Engineering vol. 3 (2009), 25-35.*
International Search; International Application No. PCT/US 12/68433; Date of Mailing Feb. 15, 2013; 11 pages.

* cited by examiner

*Primary Examiner* — Susan Tran
(74) *Attorney, Agent, or Firm* — Schmeiser, Olsen & Watts, LLP

(57) ABSTRACT

A nanoformulation that includes loaded nanoparticles. Each nanoparticle includes a modified chitosan polymer encapsulating at least one vitamin D derivative, at least one vitamin D metabolite, or combinations thereof. The modified chitosan polymer includes chitosan covalently linked to at least one entity selected from the group consisting of fatty acids (omega-3-fattay acids), amino acids, deoxycholic acid, alginate, arginine-alginate, hyaluronic acid, collagen, collagen-hydroxyapatite, poly(lactic-co-glycolic acid) (PLGA), and combinations thereof. A structure includes a medium and the nanoformulation, wherein the nanoparticles are dispersed in the medium. A method of using the nanoformulation to treat a disorder and improve efficacy of current therapies where resistance develop in a patient includes administering to the patient a therapeutically effective amount of the nanoformulation for treating the disorder. A nano-cosmetic formulation, comprising a cosmetic includes the nanoformulation, wherein the modified chitosan polymer encapsulates the at least one vitamin D derivative, and wherein the at least one vitamin D derivative encompasses 0.1 to 20.0 wt % of the nano-cosmetic formulation's total weight.

27 Claims, 2 Drawing Sheets

NANOFORMULATION OF VITAMIN D DERIVATIVES AND/OR VITAMIN D METABOLITES

RELATED APPLICATION

The present invention claims priority to U.S. Provisional No. 61/568,674, filed on Dec. 9, 2011, which is incorporated herein by reference in its entirety.

TECHNICAL FIELD

The present invention relates generally to nanoformulations, and more specifically to nanoformulations of vitamin D derivatives and/or vitamin D metabolites.

BACKGROUND

A major biologic function of vitamin D is to maintain normal blood levels of calcium and phosphorus. Vitamin D plays an important role in maintaining skeletal calcium balance by promoting calcium absorption in the intestines, promoting bone resorption by increasing osteoclast number, maintaining calcium and phosphate levels for bone formation, and allowing proper functioning of parathyroid hormone to maintain serum calcium levels. Vitamin D exists in several different forms (vitamin $D_1$ through $D_5$); the major forms are c vitamin $D_2$ (ergocalciferol) and vitamin $D_3$ (cholecalciferol). Vitamin $D_3$ is produced photochemically in the skin in the presence of certain wavelengths of light. The precursor molecule, 7-dehydrocholesterol, is produced in relatively large quantities in human skin and when it reacts with UVB light (in the 270-300 nm wavelength range), and yields previtamin $D_3$, which spontaneously isomerizes to vitamin $D_3$. The metabolism of vitamin D in humans involves two major metabolic steps. First, the liver readily modifies vitamin D to produce 25-hydroxyvitamin D, which has little activity. Subsequently, the kidney metabolizes 25-hydroxyvitamin D into the active hormone, 1, 25-dihydroxyvitamin D. Production of 1, 25-dihydroxyvitamin D is carefully regulated by the body according to mineral requirements.

It is understood that those who do not have enough exposure to sunlight with certain ultra violet wavelengths tend to suffer from vitamin D deficiency (hypo-vitaminosis D), due to their inability to synthesize vitamin D. This health issue arises since sunlight is required for vitamin D synthesis in humans.

While vitamin D has been used as a supplement for many decades, the supplement's oral bioavailability dynamics are not well understood. In addition, vitamin D is known to have impaired oral absorption in individuals with biliary or hepatic dysfunction or fat mal-absorption syndromes. Further, the generation of the active metabolites 25hydroxyvitamin D and 1,25dihydroxyvitamin D are impaired in renal and hepatic disorders.

BRIEF SUMMARY

The present invention provides a nanoformulation, comprising: nanoparticles, each nanoparticle comprising a modified chitosan polymer encapsulating at least one vitamin D derivative, at least one vitamin D metabolite, or combinations thereof, wherein the modified chitosan polymer comprises chitosan covalently linked to at least one entity selected from the group consisting of fatty acids (omega-3-fatty acids-EPA and/or DHA), amino acids, deoxycholic acid, alginate, arginine-alginate, hyaluronic acid, collagen, collagen-hydroxyapatite, poly(lactic-co-glycolic acid) (PLGA), and combinations thereof.

The present invention provides a structure, comprising a medium; and the nanoformulation, wherein the nanoparticles are dispersed in the medium.

The present invention provides a method of using the nanoformulation to treat a disorder in a patient, said method comprising: administering to the patient a therapeutically effective amount of the nanoformulation for treating the disorder.

The present invention provides a nano-cosmetic formulation, comprising a cosmetic that includes the nanoformulation, wherein the modified chitosan polymer encapsulates the at least one vitamin D derivative, and wherein the at least one vitamin D derivative encompasses 0.1 to 20.0 wt % of the total weight of the nano-cosmetic formulation.

The present invention provides a method of improving the response of a patient to a therapy used to treat the patient for a disorder, said method comprising administering the nanoformulation systemically to the patient to counteract resistance developed by the patient to the therapy.

DETAILED DESCRIPTION

Figure 1:
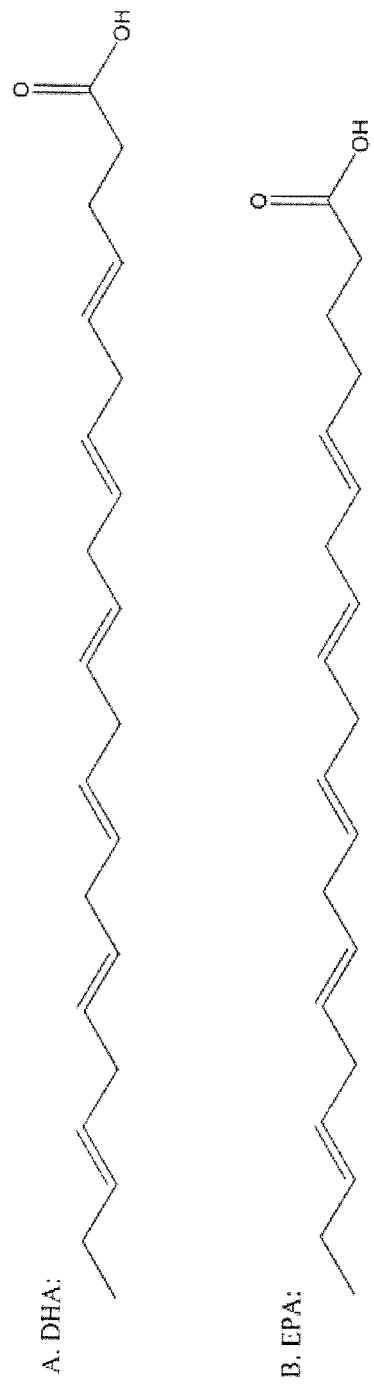
FIG. 1 depicts a chemical structure of docosahexaenoic acid (DHA), eicosapentaenoic acid (EPA), and DHA and/or EPA linked to chitosan polymer via a cleavable linker, in accordance with embodiments of the present invention.
Figure 1:
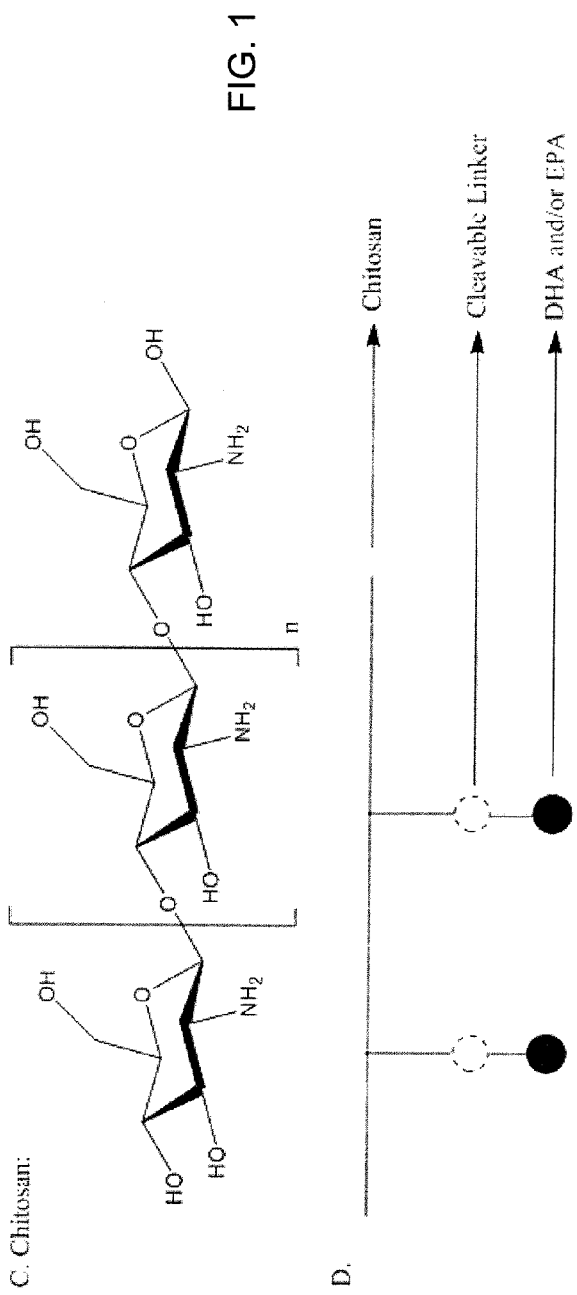

The present invention relates to formulations and methods for their manufacture and use. For example, one embodiment of the invention relates to transdermal pharmaceutical composition comprising Vitamin D (D1-D5, and/or metabolites) and preferably D3 nanoformulations to be dispersed in polyethylene glycol (PEG), poly oxy ethylene-glyceryl-tri-fatty acids (POEG), water resistance thin film forming cellulose polymer bridged by ethyl or ethoxy ether linkage, silicone gel, and other liquid gel for use in the manufacture of transdermal pharmaceutical compositions for skin application. Nanoformulations to be used include hydrophobically modified chitosan (chitosan-fatty acids, amino acids, hyaluronic acid, aliginic acids, collagen, and other cross-linkers) incorporating Vitamin D derivatives and/or its 25 hydroxy or 1, 25 hydroxy forms. These Nanoformulated Vitamin D forms listed above can also be formulated for oral delivery as a solid dosage form or as an emulsion. These novel nanoformulations will be used for treating various disorders including osteoporosis, skin aging, psoriasis, and other vascular/cardiovascular disorders. These Vitamin D nanoformulations forms can include other active substances in the treatment of the above disorders, such as corticosteroids, estradiol, vitamin E, minerals, known anti-osteoporosis, psoriasis, anti-aging, vasodilators, and other known agents for the disorders listed.

Reference to vitamin D in the present application is intended to cover all forms of vitamin D, their derivatives and metabolites, and any combination therein. Because vitamin D is highly susceptible to oxidation, vitamin D has a short half-life and, as a result, rapid deactivation of its biologic activity occurs when exposed. To overcome this half-life problem, one feature of the present invention is the formulation of vitamin D in a way that protects the active ingredient from oxidation; such a result is achieved by encapsulating vitamin D in nanoparticles with natural antioxidants (polyphenols, isoflavones, flavones, and combinations thereof), yielding a number of novel hydrophobic nanoformulations. Nano-encapsulation to stabilize vitamin D derivatives and/or its active metabolites, namely 25 hydroxy and/or 1, 25 dihydroxyvitamin D, will enhance the efficacy of vitamin D in the management of osteoporosis, skin aging, psoriasis, vascular and cardiovascular disease, as well as a host of other health conditions.

In one embodiment, the Vitamin D derivatives may include vitamin D1 (ergocalciferol with lumisterol, 1:1) vitamin D2 (ergocalciferol), D3 (cholecalciferol), D4 (22-dihydroergocalciferol), D5 (sitocalciferol), Vitamin D precursor (7-dehydrocholesterol), or combination thereof.

In one embodiment, the Vitamin D derivatives may include pre-vitamins D2 and D3, ergosterol, 7-dehydrocholesterol, lumisterol, pyrocalciferol, isopyrocalciferol, tachysterol, and combination thereof.

In one embodiment, the Vitamin D derivatives may include calcipotriene and/or calcitriol.

In one embodiment, the Vitamin D metabolites may include 25 hydroxy and/or 1, 25 hydroxyvitamin D and preferably D3.

While these novel formulations can be administered orally, a delivery vehicle for topical or transdermal administration is presented herein as an alternative to the oral route of administration. Additionally, the Nano carriers described in accordance with the present invention are extended for improved oral delivery of vitamin D derivatives and/or metabolites. Where reference is made to vitamin D as the encapsulated molecule in this application; it is intended that any of the forms of vitamin D can be encapsulated to yield the novel formulations described herein. Further, precursors, derivatives, and/or metabolites of the different forms of vitamin D can be utilized alone or in different combinations to yield the nanoformulations described.

Because vitamin D is hydrophobic, use of hydrophilic chitosan as a Nano carrier is not useful for the present invention. Hence, the present invention modifies chitosan, making the modified chitosan hydrophobic by cross linking to various acids listed in the invention for the encapsulation of the hydrophobic vitamin D. Ultra-pure low molecular weight chitosan is conjugated (e.g., covalently linked) to fatty acids (including, but not limited to, eicosapentaenoic acid (EPA), docosahexaenoic acid (DHA), or combinations in different amounts), hyaluronic acid, leading to the generation of a hydrophobic polymer. Importantly, this conjugation allows the hydrophobic polymer to retain its muco-adhesive properties with respect to a mammal and positive charges for long residence time on cell membranes of the mammal. Such a feature is important because the efficacy of the nanoformulation is associated with the ability to associate with biological tissues. In one embodiment, the molecular weight of the chitosan is in a range of 5 to 150 kilo Daltons.

Several embodiments of the present invention were prepared by encapsulation of vitamin D into hydrophobic chitosan-EPA, chitosan-DHA or chitosan EPA/DHA nanoparticles. In another embodiment, the coating of chitosan with deoxycholate to provide for increased permeation can be carried out. Additionally, chitosan can be conjugated to other fatty acids or acids such as linolenic acid, hyaluronic acid, aliginic acid, amino acids, aliginic acids, collagen, poly(lactic-co-glycolic acid) [PLGA], or combinations thereof to generate hydrophobic nanoparticles.

The embodiment utilizing omega 3 fatty acids (for example, EPA, DHA, or combinations thereof), conjugated to chitosan to generate hydrophobic nanoparticles encapsulating vitamin D provides for additional benefits. These novel nanoparticles provide for the release of omega 3 fatty acid and vitamin D simultaneously when applied topically or administered orally.

An experimental model involving certain pig species can be utilized in order to demonstrate the efficacy of the compositions and methods of treatment claimed herein. Specifically, this model can be used to measure the relative efficacy of various nanoformulations in delivering biologically active vitamin D to the skin and, subsequently, the bloodstream. Pigs offer a closer analogy to humans in the context of skin studies than the other commonly used laboratory species. The skin of the pig bears many similarities to that of humans, except in its sweat glands. Accordingly, this animal provides for is one of the best models for studying the pharmacokinetics of these nanoformulations. Epidermal, dermal, and plasma concentrations of vitamin D and its metabolites can be measured using this model in order to determine the bioavailability of the claimed compounds in the context of both oral and topical delivery methods.

In order to undertake such a study working via the topical route of administration, a known amount of the nanoformulation is applied to the skin of the pig, followed by measurement of concentration of vitamin D or its metabolites in the skin (epidermis, dermis) and plasma. The model is effective in testing both a variety of nanoformulations of vitamin D, vitamin D derivatives as well as their active metabolites.

These pharmacokinetic studies are carried out by collecting data at a range of time points to measure the immediate impact of ingestion or topical application of the nanoformulation over minutes and hours as well as the long-term effects of long-term use over days, weeks, months, and years. For each time point, a blood sample is drawn and the plasma separated. For analysis of the skin, micro-extraction probes can be used to obtain a tissue sample for analysis.

FIG. 1 depicts a chemical structure of docosahexaenoic acid (DHA), eicosapentaenoic acid (EPA), and DHA and/or EPA linked to chitosan polymer via a cleavable linker, in accordance with embodiments of the present invention. In one embodiment, the number of repeating units (n) of a chitosan structural group in the chitosan polymer in FIG. 1 is in a range of 30<n<1000, or more particularly in a range of 30<n<300.

In FIG. 1, DHA, EPA or DHA/EPA are conjugated to, by being cross-linked or covalently linked to, chitosan polymer through a cleavable linker, which can be cleaved to release the DHA/EPA and vitamin D, vitamin D metabolites, derivatives, and/or analogs thereof, under physiological conditions. A vitamin D analog is structurally similar to vitamin D, but differing from vitamin D in one or more atoms, functional groups, or substructures, which are replaced with other atoms, groups, or substructures. Conjugations of chitosan polymer separately to other small molecules or polymers have been demonstrated. Thus, the concept of making cleavable link between the polymer (chitosan) and DHA, EPA or DHA/EPA is applied herein. The cleavable linkage to chitosan polymer in FIG. 1 can be explained in terms of the following repeating unit portion of the chemical structure of chitosan in FIG. 1 in which the top branch from the ring structure terminating in OH is $CH_2OH$. The COOH groups (in the EPA and/or DHA) and the $NH_2$ (in the chitosan) lead to formation of an amide bond (—CO—NH—), and/or the COOH of EPA/DHA and the $CH_2OH$ of chitosan leading to generation of an ester bond (—COO—$CH_2$—), wherein the amide bond and the ester bond are biodegradable to different degrees.

Figure 2:
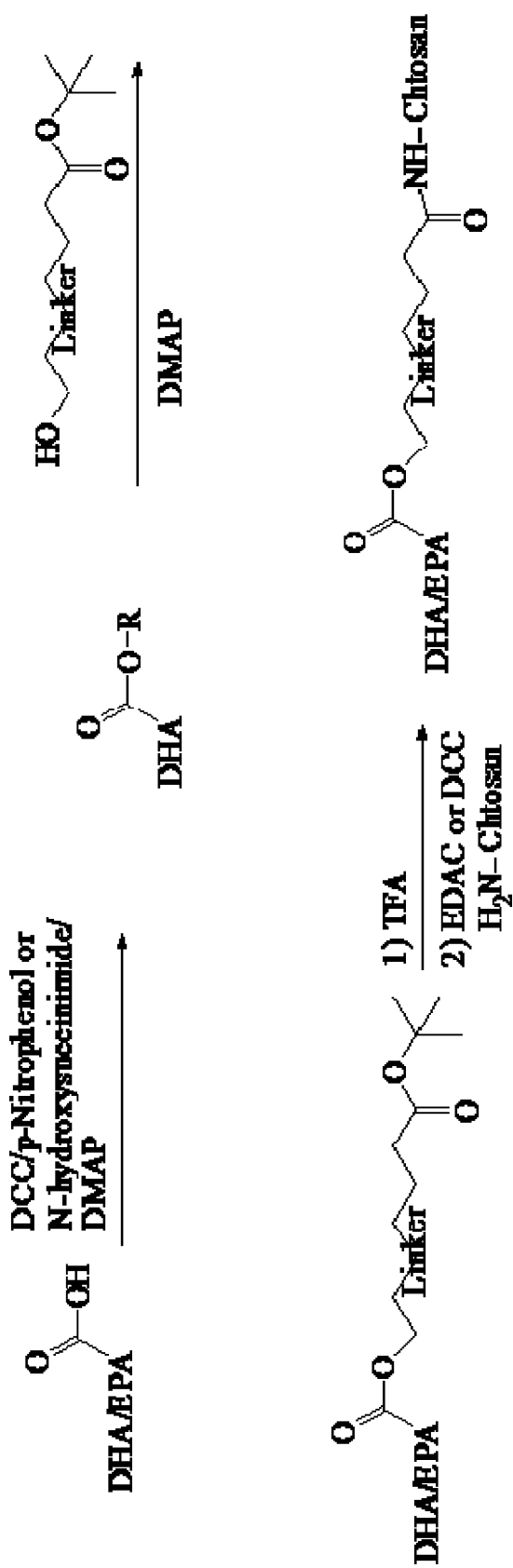
FIG. 2 is a schematic diagram showing the chemical reactions involved in the synthesis of EPA, DHA, EPA/DHA, linolenic acid, and aliginic acid chitosan polymer, in accordance with embodiments of the present invention.

FIG. 2 is a schematic diagram showing the chemical reactions involved in the synthesis of EPA, DHA, EPA/DHA, linolenic acid, and aliginic acid chitosan polymer, in accordance with embodiments of the present invention. The same procedure applied for chitosan conjugation to fatty acids, amino acids, hyaluronic acid, and other acids. DHA/EPA-chitosan nanoparticles incorporating vitamin D, vitamin D metabolites, derivatives, and/or their analogs are synthesized by gelation of chitosan with tripolyphophate (TPP) by ionic cross-linking. Briefly, an amount of DHA/EPA-chitosan is combined with an amount of vitamin D, vitamin D metabolites, derivatives, and/or analogs thereof. To this solution, an amount of TPP is added. After cross-linking, the nanoparticles are isolated by centrifugation. The size of the nanoparticles is determined by dynamic light scattering instrument (DLS) and transmission electron microscopy (TEM). Loading efficiency is determined by high performance liquid chromatography (HPLC). Similarly, chitosan or can be cross-linked with fatty acids, linolenic acid, or aliginic acid, generating nanoparticles for encapsulation of vitamin D derivatives, and/or metabolites (see FIG. 3). In an another embodiment, the chitosan can be coated with deoxycholate.

Size measurement were obtained of chitosan-EPA and/or DHA nanoparticles incorporating Vitamin D3 or 25 hydroxy D3 using dynamic laser light scattering (DLS) instrument, which demonstrated an average size of nanoparticle generated in the range of 50-250 nm and zeta potential of 5-25 mV.

The in vitro release kinetics of nanoparticles generated in the above-described process can be measured to ensure proper synthesis and biological efficacy. The release kinetics of DHA/EPA and vitamin D (including metabolites, derivatives, and/or analogs thereof) from chitosan or chitosan/deoxycholate nanoparticles is studied in phosphate buffered saline (PBS, pH 7.4), simulated gastric fluid (SGF, pH 1.2), simulated intestinal fluid (SIF, pH 7.5), human plasma or human serum albumin (HSA). A known amount of DHA/EPA containing vitamin D (including metabolites, derivatives, and/or analogs thereof) conjugated to the nanoparticles will be suspended with 20 ml of various media as mentioned above and the solutions will be kept at room temperature. At various time intervals, an amount of the suspension containing DHA/EPA-chitosan nanoparticles encapsulating vitamin D is taken out and centrifuged for 20 minutes at 10,000×g to separate the released DHA/EPA and vitamin D (D2, D3, metabolites, derivatives, and/or analogs thereof) from the nanoparticles. The centrifugates containing the released DHA/EPA and vitamin D are analyzed by HPLC.

In another embodiment of the invention, the chitosan is conjugated to deoxycholic acid. Briefly, chitosan polymer is conjugated to deoxycholic acid using carbodiimde chemistry via a covalent bond between the —NH2 and —COOH group present in chitosan and deoxycholic acid respectively. Subsequently, this hybrid polymer can used to synthesize chitosan-deoxycholic acid nanoparticles (CH-DA-NPs) incorporating vitamin D (see FIGS. 2 and 3).

For topical application, these vitamin D nanoformulations can be dispensed in polyethylene glycol (PEG), poly oxy ethylene-glyceryl-tri-fatty acids (POEG), water resistant thin film forming cellulose polymer bridged by ethyl or ethoxy ether linkage, silicone gel, or any other medium known or used for cosmetic or medical topical applications.

The loading ability of hydrophobically-modified chitosan (using chitosan-fatty acids, amino acids, hyaluronic acid, deoxycholic acid, aliginic acids, collagen, and/or other cross-linkers) is also used for the incorporation of vitamin D derivatives and/or its 25 hydroxy or 1, 25 hydroxy forms. Thus the nanoformulation of the present invention may comprise a modified chitosan polymer encapsulating at least one vitamin D derivative, at least one vitamin D metabolite, or combinations thereof. The modified chitosan polymer may comprise chitosan covalently linked to at least one entity selected from the group consisting of fatty acids, amino acids, deoxycholate, alginate, arginine-alginate, collagen, collagen-hydroxyapatite, poly(lactic-co-glycolic acid) (PLGA), and combinations thereof.

The modified chitosan polymer may be hydrophobic.

The modified chitosan polymer may comprise chitosan covalently linked to the fatty acids, wherein the fatty acids are selected from the group consisting of eicosapentaenoic acid (EPA), docosahexaenoic acid (DHA), linolenic acid, hyaluronic acid, and combinations thereof.

The modified chitosan polymer may encapsulate the at least one vitamin D derivative, wherein the at least one vitamin D derivative is selected from the group consisting of vitamin D1 (ergocalciferol with lumisterol in a 1:1 ratio), vitamin D2 (ergocalciferol), D3 (cholecalciferol), D4 (22-dihydroergocalciferol), D5 (sitocalciferol), pre-vitamin D2, pre-vitamin D3, ergosterol, 7-dehydrocholesterol, lumisterol, pyrocalciferol, isopyrocalciferol, tachysterol, calcipotriene, calcitriol, and combination thereof.

The modified chitosan polymer may encapsulate the at least one vitamin D metabolite, wherein the at least one vitamin D metabolite is selected from the group consisting of 25 hydroxyvitamin D, (1, 25 hydroxyvitamin D), and combinations thereof.

The chitosan may be covalently linked to the at least one entity by a respective cleavable linker. The respective cleavable linker may link $NH_2$ group or a $CH_2OH$ group in the chitosan to an entity of the at least one entity within the conjugate such EPA/and or DHA.

The chitosan may comprise n repeating units of a chitosan structural group, wherein n is in a range of 30<n<1000.

The chitosan may comprise a molecular weight in a range of 5 to 150 kilo Daltons.

The nanoformulation may be configured to be applied topically or delivered orally to a mammal. The modified chitosan polymer may have muco-adhesive properties with respect to the mammal.

In one embodiment, the nanoformulations listed below in a)-n) can be dispersed in a medium selected from the group consisting of polyethylene glycol (PEG), poly oxy ethylene-glyceryl-tri-fatty acids (POEG), water resistant thin film forming cellulose polymer bridged by ethyl or ethoxy ether linkage, silicone gel, and combinations thereof. Moreover, the vitamin nanoformulations listed below in a)-n) can be dispersed in any other liquid gel for use in the manufacture of transdermal pharmaceutical compositions for skin applications. In one embodiment, the modified chitosan polymer of the present invention encapsulates at least one vitamin D derivative, wherein the at least one vitamin D derivative has a concentration of 0.01-10 mg/ml in the preceding medium. A structure of the present invention may comprise the preceding medium in which the nanoformulation of the present invention is dispersed and may include any of the nanoformulations listed below in a)-n).

a) Chitosan-EPA, DHA, or EPA/DHA nanoparticles encapsulating vitamin D (metabolites, derivatives, and/or analogs) dispensed in PEG, POEG, water resistance thin film forming cellulose polymer bridged by ethyl or ethoxy ether linkage, silicone gel, or combinations thereof;

b) Chitosan-deoxycholate nanoparticles encapsulating vitamin D (metabolites, derivatives, and/or analogs) dispensed in PEG, POEG, water resistance thin film forming cellulose polymer bridged by ethyl or ethoxy ether linkage, silicone gel, or combinations thereof;

c) Chitosan-alginate (CS-AL-NPs) nanoparticles encapsulating vitamin D (metabolites, derivatives, and/or analogs) dispensed in PEG, POEG, water resistance thin film forming cellulose polymer bridged by ethyl or ethoxy ether linkage, or silicone gel, or combinations thereof;

d) Chitosan-arginine (CS-A-NPs)—alginate nanoparticles encapsulating vitamin D (metabolites, derivatives, and/or analogs) dispensed in PEG, POEG, water resistance thin film forming cellulose polymer bridged by ethyl or ethoxy ether linkage, silicone gel, or combinations thereof;

e) Chitosan-linolenic acid nanoparticles: chitosan is modified by coupling with linolenic acid through the 1-ethyl-3-(3-dimethylaminopropyyl) carbodiimide-mediated reaction;

f) Chitosan-hyaluronic acid nanoparticles encapsulating vitamin D (metabolites, derivatives, and/or analogs) dispensed in PEG, POEG, water resistance thin film forming cellulose polymer bridged by ethyl or ethoxy ether linkage, silicone gel, or combinations thereof;

g) Chitosan-collagen-hydroxyapatite (CL-HA NPs)—alginate nanoparticles encapsulating vitamin D (metabolites, derivatives, and/or analogs) dispensed in PEG, POEG, water resistance thin film forming cellulose polymer bridged by ethyl or ethoxy ether linkage, or silicone gel, or combinations thereof;

h) Chitosan-PLGA {poly(lactic-co-glycolic acid)} nanoparticles encapsulating vitamin D (derivatives and/or metabolites) dispensed in PEG, POEG, water resistance thin film forming cellulose polymer bridged by ethyl or ethoxy ether linkage, silicone gel, or combination thereof;

i) Chitosan-EPA, DHA, EPA/DHA, and hyaluronic acid nanoparticles encapsulating vitamin D (derivatives and/or metabolites) dispensed in PEG, POEG, water resistance thin film forming cellulose polymer bridged by ethyl or ethoxy ether linkage, silicone gel, or combination thereof;

j) Chitosan-EPA, DHA, EPA/DHA, and aliginic acid nanoparticles encapsulating vitamin D (derivatives and/or metabolites) dispensed in PEG, POEG, water resistance thin film forming cellulose polymer bridged by ethyl or ethoxy ether linkage, silicone gel, or combination thereof;

k) Chitosan-EPA, DHA, EPA/DHA, and PLGA nanoparticles encapsulating vitamin D (derivatives and/or metabolites) dispensed in PEG, POEG, water resistance thin film forming cellulose polymer bridged by ethyl or ethoxy ether linkage, silicone gel, or combination thereof;

l) Chitosan-EPA/DHA Nanoparticles coated with chitosan and/or chitosan deoxycholate encapsulating vitamin D (derivatives and/or metabolites) dispensed in PEG, POEG, water resistance thin film forming cellulose polymer bridged by ethyl or ethoxy ether linkage, silicone gel or combination thereof;

m) PLGA {poly(lactic-co-glycolic acid)} nanoparticles coated with chitosan and/or chitosan deoxycholate encapsulating vitamin D (derivatives and/or metabolites) dispensed in PEG, POEG, water resistance thin film forming cellulose polymer bridged by ethyl or ethoxy ether linkage, silicone gel, or combination thereof;

n) Collagen-hydroxyapatite (CL-HA NPs)—alginate Nanoparticles coated with chitosan and/or chitosan deoxycholate encapsulating vitamin D (derivatives and/or metabolites) dispensed in PEG, POEG, water resistance thin film forming cellulose polymer bridged by ethyl or ethoxy ether linkage, silicone gel, or combination thereof.

In one embodiment, a structure of the present invention comprises a medium and the inventive nanoformulation, wherein the nanoparticles of the nanoformulation are dispersed in the medium, wherein the medium is a tablet, a capsule, or an emulsion, or injectable wherein the modified chitosan polymer encapsulates at least one vitamin D derivative, and wherein the at least one vitamin D derivative may have a concentration of 0.01-10 mg/ml in the medium.

An effective amount of a composition comprising any of the nanoformulations described herein for the present invention may be administered (e.g., applied topically or delivered orally) to a mammal (e.g., a patient) for various purposes such as, inter alia, treatment of a disorder (e.g., osteoporosis, skin aging, psoriasis), vascular/cardiovascular benefits, cosmetic benefits, etc.

A systemic use of the nanoformulation of the present invention would have major benefits in improving the pharmacokinetic and pharmacodynamics properties of Vitamin D and its utility for improving the response of a patient to a therapy used to treat the patient for a disorder. The nanoformulation may be administered to the patients systemically to counteract resistance developed by the patient to the therapy. The disorder may be, inter alia, cancer, viral infection, hepatitis B, hepatitis C, and/or diabetes.

When delivered orally, the composition may be formulated in a solid dosage form as a tablet, capsule, or emulsion. In one embodiment, the composition comprises 0.01-10 mg/ml, vitamin D derivatives.

In one embodiment, the nanoformulation may be a nano-cosmetic formulation having an amount of the vitamin D and derivatives from 0.1 to 20.0 wt %, as solid, based on total weight of the nano-cosmetic formulation. The nano-cosmetic formulation may be a cosmetic in the form of cream, ointment, shampoo or rinse. The nano-cosmetic formulation may be applied topically to deliver a therapeutic amount of vitamin D derivatives to the blood of a mammal using a suitable nano-carrier.

The present invention provides a method of using the nanoformulation of the present invention to treat a disorder in a patient, which includes administering to the patient a therapeutically effective amount of the nanoformulation for treating the disorder. The In one embodiment, the disorder may be osteoporosis, skin aging, psoriasis, a vascular disorder, cardiovascular disorder, cancer, and infectious diseases. The administering of the therapeutically effective amount of the nanoformulation may comprise applying the nanoformulation topically to the patient or delivering the nanoformulation orally to the patient.

The present invention provides a nano-cosmetic formulation, comprising a cosmetic that includes the nanoformulation of the present invention, wherein the modified chitosan polymer encapsulates at least one vitamin D derivative, and wherein the at least one vitamin D derivative may encompass 0.1 to 20.0 wt % of the total weight of the nano-cosmetic formulation. The cosmetic may be in a form of cream, ointment, shampoo, or rinse.

While particular embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A nanoformulation, comprising:
nanoparticles, each nanoparticle comprising a modified chitosan polymer encapsulating at least one vitamin D derivative, at least one vitamin D metabolite, or combinations thereof,
wherein the modified chitosan polymer comprises chitosan covalently linked to at least one entity selected from the group consisting of fatty acids, amino acids, deoxycholate, alginate, arginine-alginate, collagen, collagen-hydroxyapatite, poly(lactic-co-glycolic acid) (PLGA), and combinations thereof,
wherein the modified chitosan polymer is hydrophobic, and wherein the chitosan comprises a molecular weight in a range of 5 to 150 kilo Daltons.

2. The nanoformulation of claim 1, wherein the modified chitosan polymer comprises chitosan covalently linked to the fatty acids, and wherein the fatty acids are selected from the group consisting of eicosapentaenoic acid (EPA), docosahexaenoic acid (DHA), linolenic acid, hyaluronic acid, and combinations thereof.

3. The nanoformulation of claim 1, wherein the modified chitosan polymer encapsulates the at least one vitamin D derivative, and wherein the at least one vitamin D derivative is selected from the group consisting of vitamin D1 (ergocalciferol with lumisterol in a 1:1 ratio), vitamin D2 (ergocalciferol), D3 (cholecalciferol), D4 (22-dihydroergocalciferol), D5 (sitocalciferol), pre-vitamin D2, pre-vitamin D3, ergosterol, 7-dehydrocholesterol, lumisterol, pyrocalciferol, isopyrocalciferol, tachysterol, calcipotriene, calcitriol, and combination thereof.

4. The nanoformulation of claim 1, wherein the modified chitosan polymer encapsulates the at least one vitamin D metabolite, and wherein the at least one vitamin D metabolite is selected from the group consisting of 25 hydroxyvitamin D, (1, 25 hydroxyvitamin D), and combinations thereof.

5. The nanoformulation of claim 1, wherein the chitosan is covalently linked to the at least one entity by a respective cleavable linker, and wherein the respective cleavable linker cleavably links a $NH_2$ group or a $CH_2OH$ group in the chitosan to an entity of the at least one entity.

6. The nanoformulation of claim 1, wherein the nanoformulation is configured to be applied topically or delivered orally to a mammal.

7. The nanoformulation of claim 6, wherein the modified chitosan polymer has muco-adhesive properties with respect to the mammal.

8. The nanoformulation of claim 1, wherein the modified chitosan polymer encapsulates at least one antioxidant selected from the group consisting of a polyphenol, an isoflavone, a flavone, and combinations thereof.

9. A structure, comprising:
a medium; and
the nanoformulation of claim 1, wherein the nanoparticles are dispersed in the medium.

10. The structure of claim 9, wherein the medium is selected from the group consisting of polyethylene glycol (PEG), poly oxy ethylene-glyceryl-tri-fatty acids (POEG), water resistant thin film forming cellulose polymer bridged by ethyl or ethoxy ether linkage, and silicone gel.

11. The structure of claim 10, wherein the modified chitosan polymer encapsulates at least one vitamin D derivative, and wherein the at least one vitamin D derivative has a concentration of 0.01-10 mg/ml in the medium.

12. The structure of claim 9, wherein the medium is selected from the group consisting of a tablet, a capsule, and an emulsion, wherein the modified chitosan polymer encapsulates at least one vitamin D derivative, and wherein the at least one vitamin D derivative has a concentration of 0.01-10 mg/ml in the medium.

13. The structure of claim 9, wherein the nanoparticles are selected from the group consisting of eicosapentaenoic acid (EPA) nanoparticles, docosahexaenoic acid (DHA) nanoparticles, chitosan-deoxycholate nanoparticles, chitosan-alginate nanoparticles, chitosan-arginine-alginate nanoparticles, chitosan-linolenic acid nanoparticles, chitosan-hyaluronic acid nanoparticles, chitosan-collagen-hydroxyapatite nanoparticles, chitosan-poly(lactic-co-glycolic acid) (PLGA) nanoparticles, and combinations thereof.

14. A method of treating a disorder in a patient, said method comprising:
administering to the patient a therapeutically effective amount of the nanoformulation of claim 1 for treating the disorder.

15. The method of claim 14, wherein the disorder, is selected from the group consisting of osteoporosis, skin aging, psoriasis, a vascular disorder, cardiovascular, cancer, and infectious disorders.

16. The method of claim 14, wherein said administering comprises applying the nanoformulation topically to the patient or delivering the nanoformulation orally to the patient.

17. A nano-cosmetic formulation, comprising a cosmetic that includes the nanoformulation of claim 1, wherein the modified chitosan polymer encapsulates at least one vitamin D derivative, and wherein the at least one vitamin D derivative encompasses 0.1 to 20.0 wt % of the total weight of the nano-cosmetic formulation.

18. The nano-cosmetic formulation of claim 17, wherein the cosmetic is in a form of cream, ointment, shampoo, or rinse.

19. A method of treating a patient for a disorder, said method comprising:
administering the nanoformulation of claim 1 systemically to the patient to counteract resistance developed by the patient to the therapy.

20. The method of claim 19, wherein the disorder is selected from the group consisting of cancer, viral infection, hepatitis B, hepatitis C, diabetes, and combinations thereof.

21. The nanoformulation of claim 1, wherein the modified chitosan polymer comprises chitosan covalently linked to the amino acids.

22. The nanoformulation of claim 1, wherein the modified chitosan polymer comprises chitosan covalently linked to the deoxycholate.

23. The nanoformulation of claim 1, wherein the modified chitosan polymer comprises chitosan covalently linked to the alginate.

24. The nanoformulation of claim 1, wherein the modified chitosan polymer comprises chitosan covalently linked to the arginine-alginate.

25. The nanoformulation of claim 1, wherein the modified chitosan polymer comprises chitosan covalently linked to the collagen.

26. The nanoformulation of claim 1, wherein the modified chitosan polymer comprises chitosan covalently linked to the collagen-hydroxyapatite.

27. The nanoformulation of claim 1, wherein the modified chitosan polymer comprises chitosan covalently linked to the PLGA.

* * * * *